United States Patent [19]

Suzuki et al.

[11] 4,245,550
[45] Jan. 20, 1981

[54] ELECTRONIC AIR CLEANER FOR PASSENGER COMPARTMENT OF VEHICLE

[75] Inventors: Kazuhiko Suzuki, Yokosuka; Masazumi Sone, Yokohama; Yukitsugu Fukumori, Yokohama; Kazuo Hayashi, Yokohama, all of Japan

[73] Assignee: Nissan Motor Company, Limited, Japan

[21] Appl. No.: 28,866

[22] Filed: Apr. 10, 1979

[30] Foreign Application Priority Data

Aug. 25, 1978 [JP] Japan .......................... 53/115803[U]

[51] Int. Cl.³ .......................... B60H 3/06; B03C 3/38
[52] U.S. Cl. ....................... 98/2.11; 55/102; 55/126; 55/146; 55/276; 55/279; 55/385 B; 422/121
[58] Field of Search ................ 55/102, 126, 134, 146, 55/279, 124, 276, 385 A, 385 B; 98/2.11; 250/455, 504, 515; 422/121, 240, 241

[56] References Cited

U.S. PATENT DOCUMENTS

| | | | |
|---|---|---|---|
| 2,405,987 | 8/1946 | Arnold | 250/515 |
| 2,434,980 | 1/1948 | Bilofsky | 250/504 |
| 2,928,941 | 3/1960 | Hicks et al. | 55/102 |
| 3,178,255 | 4/1965 | Neuwald et al. | 422/121 |
| 3,827,862 | 8/1974 | Berlant | 422/121 |
| 3,844,741 | 10/1974 | Dimitrik | 55/102 |
| 4,133,652 | 1/1979 | Ishikawa et al. | 55/126 |

FOREIGN PATENT DOCUMENTS

| | | | |
|---|---|---|---|
| 1176289 | 8/1964 | Fed. Rep. of Germany | 250/515 |
| 1240121 | 5/1967 | Fed. Rep. of Germany | 250/515 |
| 2614849 | 10/1976 | Fed. Rep. of Germany | 250/504 |

*Primary Examiner*—David L. Lacey
*Attorney, Agent, or Firm*—Lowe, King, Price & Becker

[57] ABSTRACT

An electronic air cleaner having therein an electrostatic precipitator and an ultraviolet sterilizing lamp is positioned close to an antenna of a radio receiver. A shielding cover lined with a thin metal film covers the lamp to block radiation of the electric noise waves generated by the lamp.

3 Claims, 5 Drawing Figures

FIG. 3 *(PRIOR ART)*
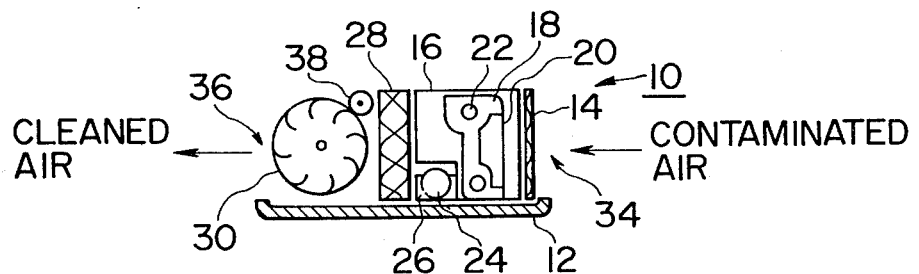
FIG. 4
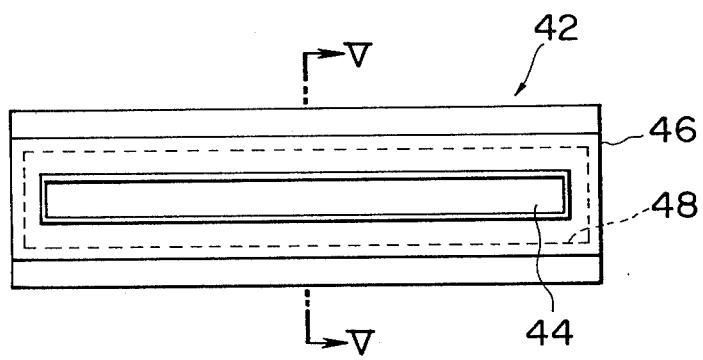
FIG. 5
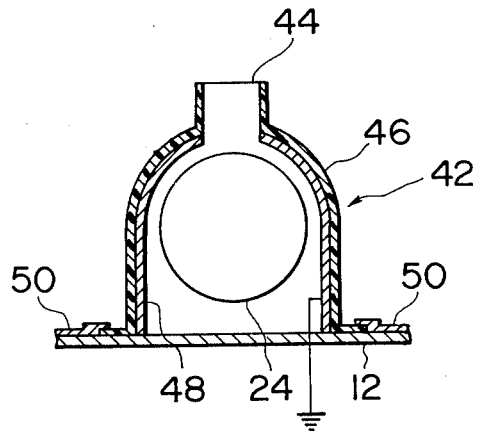

ELECTRONIC AIR CLEANER FOR PASSENGER COMPARTMENT OF VEHICLE

FIELD OF THE INVENTION

The present invention relates in general to an electronic air cleaner and more particularly to an electronic air cleaner equipped in a passenger compartment of a motor vehicle for cleaning the air in the compartment. More specifically, the present invention is concerned with an improvement in construction of the electronic air cleaner for suppressing the radio-interference caused by it.

BACKGROUND OF THE INVENTION

For cleaning or purifying the air in the passenger compartment of a vehicle, many kinds of electronic air cleaner equipped with a so-called electrostatic precipitator have been used. Some of these cleaners have therein air sterilizing means (such as an ultraviolet sterilizing lamp), air deodorizing means (such as an activated charcoal filter) and negative ion generating means for providing the passengers in the compartment with comfortable ride. However, in such electric cleaners, considerable amounts of electric noise waves tend to leak out from the cleaner especially from the ultraviolet sterilizing lamp. Such noise waves interfere with other electric devices of the vehicle, such as radio receiver, in a great degree. Especially, as viewed in FIG. 1, if such electronic air cleaner "A" with the ultraviolet lamp is set at a position close to an antenna "B" of the radio receiver, the interference by the noise waves becomes most critical. In fact, for achieving smooth air flow in the passenger compartment of the vehicle, the cleaner is used to be set on a rear parcel shelf "C" even if the antenna of the radio receiver is attached to or immersed in a rear window pane "D", as shown.

OBJECTS OF THE INVENTION

It is therefore an object of the present invention to provide an improved electronic air cleaner which is constructed and designed to suppress leakage of electric noise waves therefrom.

It is another object of the present invention to provide an electronic air cleaner which has a shielding cover for an ultraviolet sterilizing lamp installed therein for blocking radiation of the unwanted electric noise waves generated by the lamp.

SUMMARY OF THE DRAWINGS

Other objects and advantages of the present invention will become clear from the following description when taken in conjunction with the accompanying drawings, in which:

FIG. 3 is a sectional view taken along the line III—III of FIG. 2;

FIG. 4 is a plan view of a shielding cover for an ultraviolet sterilizing lamp, the cover constituting part of the electronic air cleaner of the invention; and FIG. 5 is a sectional view taken along the line V—V of FIG. 4.

DESCRIPTION OF THE PRIOR ART

Figure 1:
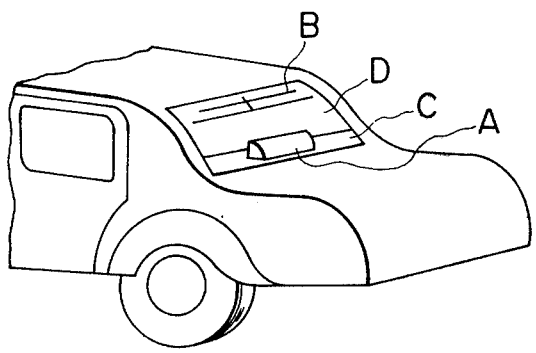
FIG. 1 is a partial sketch of a passenger motor vehicle having an electronic air cleaner setting on a rear parcel shelf near a rear window pane to or in which an antenna of a radio receiver is attached or immersed.
Figure 2:
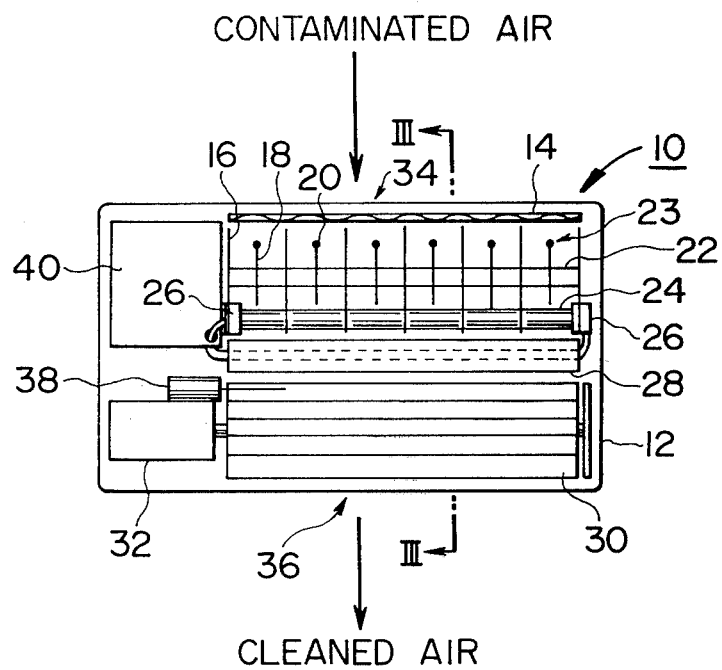
FIG. 2 is a plan view of a conventionally used electronic air cleaner with an upper lid being removed.

Referring to FIGS. 2 and 3, there is illustrated a conventionally used electronic air cleaner which is set in a passenger compartment of a vehicle.

In these figures numeral 12 denotes a base member on which a cover or lid (not shown) is set. Standing on one side of the base member 12 is a pre-filter 14 of metal wire netting. The filter 14 is held at the grounded potential and removes coarse dust particles suspended in air flowing into the cleaner 10. Positioned inside the filter 14 are grounded parallel and equally spaced electrodes 16 (only one is numbered) each consisting of a conductor plate extending inwardly at right angles with respect to the filter 14, as is understood from FIG. 2. A plurality of support plates 18 (only one is numbered) are juxtaposed within the grounded electrodes 16 such that each support plate 18 is spacedly disposed between adjacent two of the grounded electrodes 16. The support plates 18 are also constructed of a conductive material. Supported by and connected to the support plates 18 are high voltage electrodes 20 (only one is numbered) which extend generally perpendicularly to the base member 12, as is seen from FIG. 3. Designated by numeral 22 is an insulating rod by which the grounded electrodes 16 and the support plates 18 are supported so as to be electrically insulated from each other. Although not shown in the drawings, the grounded electrodes 16 are electrically connected to each other and to the body of the vehicle. The high voltage electrodes 20 are electrically connected to each other. With this, a so-called electrostatic precipitator 23 is formed.

Positioned inside the support plates 18 and near the base member 12 is an ultraviolet sterilizing lamp 24 which is supported by sockets 26. A deodorizing filter 28 including a metal wire net bag and activated charcoal or catalyzer in the bag is placed at the rear of the ultraviolet lamp 26. A cross flow fan 30 powered by an electric motor 32 is provided to take in the polluted air from an air inlet 34 and let out the cleaned or treated air to an air outlet 36. A negative ion generator 38 is positioned upstream of the fan 30. Designated by numeral 40 is an electric converter which supplies the electric devices such as the electrostatic precipitator 23, the ultraviolet lamp 24, the electric motor 32 and the negative ion generator 38, with necessary electric power. For instance, the electric to converter 40 is designed to supply A.C. 500 V to the ultraviolet lamp 24, D.C. +5 kV to the electrostatic precipitator 23 and D.C. −5 kV to the negative ion generator 38 by converting the direct current supplied by a D.C. 12 V battery.

In operation, the contaminated or polluted air in the passenger compartment is forced to flow, by the fan 30, toward the inlet opening 34 and then pass through the filter 14 to remove the coarse dust particles. The air losing the coarse dust particles is then led to the electrostatic precipitator 23 where the remaining fine dust particles are charged on the principle of electrostatic dust collection and attracted to the grounded electrodes 16 to be arrested thereon. The air losing the coarse and fine dust particles passes by the ultraviolet lamp 24 for sterilization of the air and then the air is led to the deodorizing filter 28 for elimination of smell of the air. The deodorized air is then led to the negative ion generator 38 to be fed with a negative ion. The air thus cleaned or treated is then discharged from the outlet 36 of the cleaner 10 into the passenger compartment.

In the above-mentioned cleaner 10, however, the unwanted electric noise waves tend to leak out in a considerable amount from the cleaner 10 due to lack of sufficient shielding for the noise waves generated by the ultraviolet sterilizing lamp 24.

SUMMARY OF THE INVENTION

According to the present invention, there is provided an electronic air cleaner having therein both an electrostatic precipitator for removing fine dust particles suspended in air and an ultraviolet lamp for sterilizing the air, the cleaner comprising: a cover member constructed of an electrically insulating material and having an opening, the cover member being arranged to cover the lamp with the opening facing toward the passage of air which is to be sterilized; and a metal film lined to the inner surface of said cover and grounded.

DESCRIPTION OF THE PREFERRED EMBODIMENT

Referring to FIGS. 4 and 5, there is illustrated an elongate shielding cover 42 which constitutes part of an electronic air cleaner of the present invention, the cover 42 covering the ultraviolet sterilizing lamp 24 to block radiation of the undesired electric noise waves from the lamp 24. The electronic air cleaner of the invention is substantially the same in construction and configuration as the afore-mentioned conventional cleaner 10 except the shielding cover 42. Thus, the whole view of the cleaner of the present invention is not presented, and for ease of understanding of the description, the parts substantially the same as in the conventional cleaner 10 will be explained by using the same reference numerals.

As is shown, the shielding cover 42 is constructed to have a curved section (no numeral) concentric with the ultraviolet lamp 24 which is cylindrical in shape, and a longitudinally extending collared opening 44 at the top section thereof. The shielding cover 42 comprises a base 46 made of, for instance, rigid plastics. The inside or interior surface of the base 46 is lined with a thin metal film 48 made of, for example, Aluminum (Al), Silver (Ag) or Tin (Sn). The film 48 is grounded and polished. Preferably, the film 48 is made by the vacuum evaporation method. The shielding cover 42 is secured at the lower flange sections (no numerals) thereof to the base member 12 of the cleaner 10 of the invention in such a manner that the collared opening 44 faces the passage of the air which flows from the electrostatic precipitator 23 to the deodorizing filter 28. If desired, the bottom of the shielding cover 42, more specifically, the upper surface of the base member 12 positioned in the cover 42 may be lined with the thin metal film for not only improving the noise wave shielding function thereof but also increasing intensity of ultraviolet ray directing toward the opening 44. In fact, the metal film can act as a light reflector.

In setting the electronic air cleaner 10 of the invention on the passenger vehicle, the cleaner 10 is arranged such that the collared opening 44 does not face toward the sensitive electric device, such as the antenna of the radio receiver. Thus, when the cleaner 10 is set on the rear parcel shelf "C" above which the antenna "B" attached to or immersed in the rear window pane "D" is closely located, a slight inclination of the shielding cover 42 with respect to the base member 12 may be required.

Thus, it will be appreciated that according to the present invention, the noise waves generated by the ultraviolet sterilizing lamp are prevented from scattering outwardly by the shielding cover 42 which is simple in construction and easy to assemble.

The foregoing description shows only one preferred embodiment of the invention. Various modifications are apparent to those skilled in the art without departing from the scope of the subject invention which is only limited by the appended claims. Therefore, the embodiment shown and described is only illustrative, not retrictive.

What is claimed is:

1. In a vehicle having an electric device sensitive to an electric noise wave and having an electric air cleaner for cleaning air in a passenger compartment, said cleaner being positioned close to the electrically sensitive device and comprising an electrostatic precipitator for removing fine dust particles suspended in the air, said precipitator including electrically insulated first and second groups of electrodes between which a high electric potential is applied: said cleaner further comprising an ultraviolet lamp for sterilizing the air:
   a cover member constructed of an electrically insulating material and having an opening, said cover member being arranged to cover said lamp with the opening facing away from said electrically sensitive device; and
   an electrically grounded, vacuum evaporated metal film lined to the inner surface of said cover.

2. The apparatus as in claim 1, wherein said ultraviolet lamp is cylindrical in shape and wherein said cover member is constructed to have a curved section concentric with said ultraviolet lamp.

3. The apparatus as in claim 2, wherein said opening is a longitudinally extending collared opening formed at the top of said curved section of said cover member.

* * * * *